United States Patent
Nishiyama et al.

(10) Patent No.: US 9,591,967 B2
(45) Date of Patent: Mar. 14, 2017

(54) OPTICAL TOMOGRAPHIC IMAGING DEVICE

(71) Applicant: NIDEK CO., LTD., Gamagori, Aichi (JP)

(72) Inventors: Junpei Nishiyama, Gamagori (JP); Yukihiro Higuchi, Toyota (JP)

(73) Assignee: NIDEK CO., LTD., Gamagori (JP)

( * ) Notice: Subject to any disclaimer, the term of this patent is extended or adjusted under 35 U.S.C. 154(b) by 26 days.

(21) Appl. No.: 14/865,975

(22) Filed: Sep. 25, 2015

(65) Prior Publication Data

US 2016/0113485 A1    Apr. 28, 2016

Related U.S. Application Data

(63) Continuation-in-part of application No. PCT/JP2014/057193, filed on Mar. 17, 2014.

(30) Foreign Application Priority Data

Mar. 28, 2013  (JP) ................................ 2013-068096

(51) Int. Cl.
*A61B 3/12* (2006.01)
*A61B 3/10* (2006.01)
(Continued)

(52) U.S. Cl.
CPC ........... *A61B 3/102* (2013.01); *A61B 3/0058* (2013.01); *A61B 3/14* (2013.01); *A61B 5/0066* (2013.01);
(Continued)

(58) Field of Classification Search
CPC .......... A61B 3/102; A61B 3/1225; A61B 3/14
(Continued)

(56) References Cited

U.S. PATENT DOCUMENTS

| | | | |
|---|---|---|---|
| 2007/0268456 A1* | 11/2007 | Ohbayshi | A61B 3/102 351/246 |
| 2010/0238403 A1 | 9/2010 | Kobayashi et al. | |
| 2012/0226150 A1 | 9/2012 | Balicki et al. | |

FOREIGN PATENT DOCUMENTS

| | | |
|---|---|---|
| JP | 2010-246904 A | 11/2010 |
| JP | 2013-509273 A | 3/2013 |

OTHER PUBLICATIONS

Jun. 17, 2014 International Search Report issued in International Patent Application No. PCT/JP2014/057193.
(Continued)

*Primary Examiner* — Hung Dang
(74) *Attorney, Agent, or Firm* — Oliff PLC (57) ABSTRACT

An optical tomographic imaging device configured to acquire a tomographic image of a tissue of an object, includes: a dividing device configured to divide a light beam emitted from a light source into measurement light and reference light; a combining device configured to combine the measurement light, which is separated by the dividing device and is reflected from the tissue, with the reference light so as to generate interference light for acquiring the tomographic image; a plurality of irradiation devices, each of the plurality of irradiation devices being configured to guide the measurement light and irradiate the tissue with the measurement light: and a switching device configured to switch the plurality of irradiation devices from one to another and select one of the plurality of irradiation devices to cause the selected irradiation device to irradiate the measurement light output from the dividing device with tissue.

6 Claims, 6 Drawing Sheets

(51) Int. Cl.
  *A61B 3/00*     (2006.01)
  *A61B 3/14*     (2006.01)
  *G01B 9/02*     (2006.01)
  *A61B 5/00*     (2006.01)

(52) U.S. Cl.
  CPC ..... *G01B 9/02004* (2013.01); *G01B 9/02027* (2013.01); *G01B 9/02091* (2013.01); *A61B 5/7425* (2013.01); *G01B 2290/45* (2013.01)

(58) Field of Classification Search
  USPC .................... 351/206, 246, 200, 205, 221
  See application file for complete search history.

(56) References Cited

OTHER PUBLICATIONS

Han, Shuo et al. "Handheld forward-imaging needle endoscope for ophthalmic optical coherence tomography inspection," Journal of Biomedical Optics, vol. 13(2), pp. 020505-1 to 020505-3, 2008.
Yaqoob, Zahid et al. "Methods and application areas of endoscopic optical coherence tomography," Journal of Biomedical Optics, vol. 11(6), pp. 063001-1 to 063001-19, 2006.

* cited by examiner

OPTICAL TOMOGRAPHIC IMAGING DEVICE

CROSS REFERENCE TO RELATED APPLICATION

The present application is a continuation of PCT patent application number PCT/JP2014/057193 filed on Mar. 17, 2014, which claims the benefit of Japanese Patent Application No. 2013-068096 filed on Mar. 28, 2013 the contents of which are incorporated herein by reference in its entirety.

TECHNICAL FIELD

The present invention relates to an optical tomographic imaging device which captures a tomographic image of a tissue of a test substance.

BACKGROUND ART

In the related art, there is a device using optical coherence tomography (OCT) as a device which can capture a tomographic image of a predetermined portion of a test substance. An optical tomographic imaging device using OCT divides light emitted from a light source into measurement light and reference light, and irradiates a tissue of a test substance with the separated measurement light. The measurement light reflected by the tissue is combined with the reference light, and information regarding the tissue in a depth direction is acquired on the basis of an interference signal of the combined light. The optical tomographic imaging device can generate a tomographic image by using the acquired information in the depth direction.

Various irradiation devices for irradiating a tissue with measurement light have been proposed. For example, there is an irradiation device which performs irradiation with measurement light which is applied by a galvanometer mirror. In addition, NPL 1 discloses a side imaging probe for capturing a tomographic image in a circumferential direction of the probe and a forward imaging probe for capturing a tomographic image in a tip end direction of the probe.

CITATION LITERATURE

Non Patent Literature

[NPL 1] Zahid Yaqoob, Jigang Wu, Emily J. McDowell, Xin Heng, Changhuei Yang "Methods and application areas of endoscopic optical coherence tomography" Journal of Biomedical Optics, Vol. 11, No. 6, 2006

SUMMARY OF INVENTION

Technical Problem

There is a case where a user may want to change an irradiation device used to capture a tomographic image. However, in an optical tomographic imaging device of the related art, it is unlikely to capture a tomographic image through easy change of an irradiation device.

An object of the present invention is to provide an optical tomographic imaging device which allows an irradiation device used to capture a tomographic image to be easily changed.

Solution to Problem

According to a first aspect of the present invention, there is provided an optical tomographic imaging device configured to acquire a tomographic image of a tissue of an object, the device comprising: a dividing device configured to divide a light beam emitted from a light source into measurement light and reference light; a combining device configured to combine the measurement light, which is separated by the dividing device and is reflected from the tissue, with the reference light separated by the dividing device so as to generate interference light for acquiring the tomographic image; a plurality of irradiation devices, each of the plurality of irradiation devices being configured to guide the measurement light output from the dividing device and irradiate the tissue with the measurement light: and a switching device configured to switch the plurality of irradiation devices from one to another and select one of the plurality of irradiation devices to cause the selected irradiation device to irradiate the measurement light output from the dividing device with tissue.

DESCRIPTION OF EMBODIMENT

Hereinafter, an embodiment of the present invention will be described with reference to the drawings.

Figure 1:
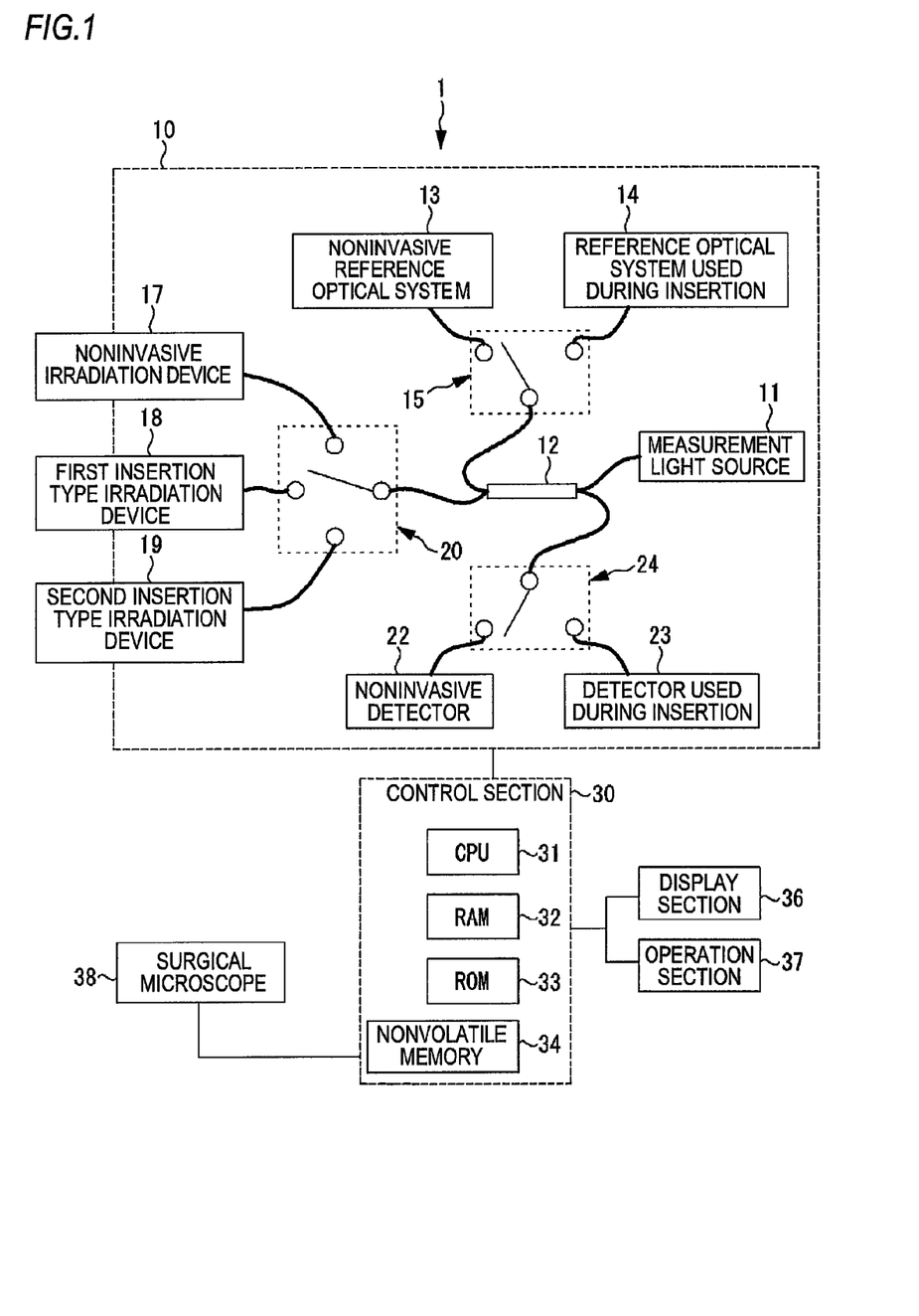
FIG. 1 is a diagram a schematic configuration of an optical tomographic imaging device 1 and peripheral devices.

First, with reference to FIG. 1, a description will be made of a schematic configuration of an optical tomographic imaging device 1 according to a preferred embodiment of the present disclosure. The optical tomographic imaging device 1 captures a tomographic image of a tissue of a test substance. In the present embodiment, a description will be made of an example of an ophthalmic imaging device which captures a tomographic image of an internal tissue (for example, the retina Ef) of a subject's eye E. However, the present invention is applicable to devices which capture a tomographic image of test objects (for example, internal organs, or the ear) other than the eye. The optical tomographic imaging device 1 includes a measurement section 10 and a control section 30.

The measurement section 10 has an optical coherence tomography (OCT) configuration. The measurement section 10 includes a measurement light source 11, a coupler 12, a noninvasive reference optical system 13, a reference optical system 14 used for during insertion, a reference light optical path switching portion 15, a plurality of irradiation devices 17 to 19, a unit switching portion 20, a noninvasive detector 22, a detector 23 used during insertion, and a detection switching portion 24. The irradiation devices 17 to 19 may be configured to be incorporated into a main body of the optical tomographic imaging device 1, and may be attached to the main body so as to be used.

The measurement light source 11 emits light for acquiring a tomographic image. As an example, the optical tomographic imaging device 1 of the present embodiment includes the measurement light source 11 which can change a wavelength of emitted laser light at a high speed, and thus acquires a tomographic image through swept-source OCT (SS-OCT) measurement. The measurement light source 11 of the present embodiment is constituted of a laser medium, a resonator, a wavelength selection filter, and the like. The wavelength selection filter may employ, for example, a combination of a diffraction grating and a polygon mirror, or a Fabry-Perot etalon.

In addition, the optical tomographic imaging device 1 includes an aiming light source (not illustrated). The aiming light source generates visible light for indicating a position irradiated with measurement light. The light generated by the aiming light source is combined with the light generated by the measurement light source 11 by using the coupler or the like.

The coupler 12 divides the light emitted from the measurement light source 11 into measurement light (sample light) and reference light. The reference light is guided to the noninvasive reference optical system 13 or the reference optical system 14 used for during insertion. The measurement light is guided to any one of the plurality of irradiation devices 17 to 19. In addition, the coupler 12 combines measurement light (reflected measurement light) reflected by the test substance and recording generated by the reference optical systems 13 and 14 so as to generate interference light. The interference light generated by the coupler 12 is guided to the noninvasive detector 22 or the detector 23 used during insertion.

The reference optical systems 13 and 14 return the recording layer guided from the coupler 12, to the coupler 12 again. The reference optical systems 13 and 14 may be of the Michelson type or the Mach-Zehnder type. In the present embodiment, the reference optical systems 13 and 14 reflect the reference light guided from the coupler 12 by using a reflection optical system including a reference mirror or the like, so as to return the reference light to the coupler 12 again. As described above, the reference light returned to the coupler 12 is combined with the reflected measurement light from the test substance. In addition, configurations of the reference optical systems 13 and 14 may be changed. For example, the reference optical systems 13 and 14 may transmit the reference light through the coupler 12 by using a transmission optical system such as an optical fiber instead of reflecting the reference light guided from the coupler 12.

In the present embodiment, the two reference optical systems (the noninvasive reference optical system 13 and the reference optical system 14 used for during insertion) are provided. An optical path length of the noninvasive reference optical system 13 is designed so as to be suitable for a case where a tomographic image is captured by the noninvasive irradiation device 17. The reference optical system 14 used for during insertion is designed so as to be suitable for a case where tomographic images are captured by the first insertion type irradiation device 18 and the second insertion type irradiation device 19.

The reference light optical path switching portion 15 is provided on a path (optical path) for connecting the reference optical systems 13 and 14 to the coupler 12. The reference light optical path switching portion 15 connects one of the two reference optical systems 13 and 14 to the coupler 12 so that the reference light is guided to the connected reference optical system. In other words, the reference light optical path switching portion 15 switches a path along which the reference light separated by the coupler 12 is actually guided between paths of the reference light respectively extending to the two reference optical systems 13 and 14. The reference light is incident to the reference optical system connected to the coupler by the reference light optical path switching portion 15, and is returned to the coupler 12 along the same path as the path along which the reference light passes during the incidence.

In addition, there is a case where a tomographic image is captured by each of the plurality of irradiation devices 17 to 19 by using a single reference optical system. In this case, the reference light optical path switching portion 15 may be omitted. Further, in a case of using a plurality of reference optical systems, needless to say, the number of reference optical systems to be used is not limited to two.

Each of the plurality of irradiation devices 17 to 19 irradiates a tissue of the test substance with the measurement light separated by the coupler 12. As will be described later in detail, the noninvasive irradiation device 17 transmits the measurement light through the cornea of the eye E which is the test substance so as to irradiate an internal tissue with the measurement light. The first insertion type irradiation device 18 is used to capture a tomographic image of a tissue located in a circumferential direction of a needle 56 (refer to FIG. 3). The second insertion type irradiation device 19 is used to capture a tomographic image of a tissue located in a tip end direction of a needle 82 (refer to FIG. 4).

The unit switching portion 20 is provided on a path (optical path) for connecting the irradiation devices 17 to 19 to the coupler 12. The unit switching portion 20 of the present embodiment connects any one of the three irradiation devices 17 to 19 to the coupler 12 so that the measurement light is guided to the connected irradiation device. In other words, the unit switching portion 20 switches an irradiation device to which the measurement light emitted from the measurement light source 11 is guided, among the plurality of irradiation devices 17 to 19. The measurement light is incident to the irradiation device connected to the coupler by the unit switching portion 20, and is applied to a tissue from the irradiation device to which the measurement light is incident. The measurement light reflected by the tissue is returned to the coupler 12 along the same path as the path along which the measurement light passes during the incidence to the irradiation device.

The detectors 22 and 23 detect an interference state between the reflected measurement light and the reference light. In other words, the detectors 22 and 23 detect an interference signal of interference light generated by the coupler 12. More specifically, in a case of Fourier domain OCT, a spectral intensity of the interference light is detected by the detectors 22 and 23. A CPU 31 which will be described later performs Fourier transform on the detected spectral intensity so as to acquire a depth profile (A scan signal) in a predetermined range. As described above, the optical tomographic imaging device 1 of the present embodiment employs SS-OCT. However, the optical tomographic imaging device 1 may employ other OCT types. For example, the optical tomographic imaging device 1 may employ either spectral-domain OCT (SD-OCT) or time-domain OCT (TD-OCT). In a case where SS-OCT is employed, balance detectors including a plurality of light receiving elements may be preferably used as the detectors 22 and 23. In a case of using the balance detectors, the optical tomographic imaging device 1 can obtain a difference between interference signals from the plurality of light receiving elements and can reduce unnecessary noise included in the interference signals. As a result, quality of a tomographic image is improved.

In the present embodiment, the two detectors (the noninvasive detector 22 and the detector 23 used during insertion) are provided. The noninvasive detector 22 is designated so as to be suitable for a case where a tomographic image is captured by the noninvasive irradiation device 17. The detector 23 used during insertion is designed so as to be suitable for a case where tomographic images are captured by the first insertion type irradiation device 18 and the second insertion type irradiation device 19.

The detection switching portion 24 is provided on an optical path for connecting the detectors 22 and 23 to the coupler 12. The detection switching portion 24 connects the coupler 12 to one of the two detectors 22 and 23 so that interference light is guided to the connected detector. In other words, the detection switching portion 24 switches a detector to which interference light generated by the coupler 12 is incident, between the two detectors.

In addition, there is a case where a tomographic image is captured by each of the plurality of irradiation devices 17 to 19 by using a single detector. In this case, the detection switching portion 24 may be omitted. Further, in a case of using a plurality of detectors, needless to say, the number of detectors to be used is not limited to two. For example, a detector which is suitable for imaging performed by the first insertion type irradiation device 18 and a detector which is suitable for imaging performed by the second insertion type irradiation device 19 may be separately provided.

The measurement section 10 has a configuration of changing an optical path length difference between measurement light and reference light. The measurement section 10 of the present embodiment changes the optical path length difference between moving optical members (for example, reference mirrors) included in the reference optical systems 13 and 14 in an optical axis direction. However, a configuration for changing the optical path length difference may be disposed on the optical path of the measurement light. In addition, the optical tomographic imaging device 1 further includes various configurations such as an optical system for performing focus adjustment of the measurement light, but a detailed description thereof will be omitted.

In the present embodiment, optical switches which change paths of light beams are used in the reference light optical path switching portion 15, the unit switching portion 20, and the detection switching portion 24. Each of the optical switches may employ any one of various configurations. For example, a mechanical type optical switch, a MEMS optical switch, or a light waveguide type optical switch may be used. The mechanical type optical switch switches an optical path by moving a mirror with an actuator. The MEMS optical switch switches an optical path by using static electricity. In the light waveguide type optical switch, a light waveguide is formed on a substrate made of silicon, polymer resin, or the like, and thin-film metal heaters are disposed on both sides of the light waveguide. In the light waveguide type optical switch, the waveguide is heated by one heater so that a temperature difference occurs in both sides of the waveguide. Thus, a light refractive index in changed on the light waveguide side, thereby allowing a light propagation path in the light waveguide to be switched. By using the optical switch, the optical tomographic imaging device 1 can easily switch a path of a light beam according to worker's applications (for example, an operator's or an examiner's applications).

The control section 30 includes a central processing unit (CPU) 31, a RAM 32, a ROM 33, a nonvolatile memory 34, and the like. The CPU 31 controls the optical tomographic imaging device 1 and peripheral devices. The RAM 32 temporarily stores various information. Various programs, initial values, and the like are stored in the ROM 33. The nonvolatile memory 34 is a non-transitory medium which can hold the stored content even if the supply of power is cut off. For example, a hard disk drive, a flash ROM, and a USB memory which is attachably and detachably attached to the optical tomographic imaging device 1 may be used as the nonvolatile memory 34. The nonvolatile memory 34 stores an imaging control program for controlling a main process (refer to FIG. 5) which will be described later. In addition, the nonvolatile memory 34 stores various data such as captured tomographic image data.

In the present embodiment, a personal computer (hereinafter, referred to as a "PC") connected to the measurement section 10 is used as the control section 30. However, instead of using the PC, the measurement section 10 and the control section 30 may be integrated into one device. In addition, the control section 30 may be configured by using a plurality of controllers (that is, a plurality of processors). For example, the control section 30 of the optical tomographic imaging device 1 may be configured by using a first controller provided in the PC and a second controller provided in the measurement section 10. In this case, for example, the first controller of the PC may give instructions for starting and ending of imaging to the second controller on the basis of an operation from an operation section connected to the PC. The second controller may control operations of the measurement light source 11, the various switches 15, 20 and 24, and the like in response to instructions from the first controller. An image generation process or the like based on an interference signal may be performed either the first control or the second controller.

The control section 30 is connected to peripheral devices such as a display section 36, an operation section 37, and a surgical microscope 38. A tomographic image or the like captured by the optical tomographic imaging device 1 is displayed on the display section 36. The display section 36 may be a display of the PC, and may be a display used for the optical tomographic imaging device 1 only. A plurality of displays may be used together. The operation section 37 is a device for inputting various operation instructions from a worker to the optical tomographic imaging device 1. As the operation section 37, for example, at least one of a mouse, a joystick, a keyboard, and a touch panel may be used. The surgical microscope 38 enlarges and displays (in the present embodiment, enlarges and displays an image of) the inside of a test object (in the present embodiment, the subject's eye E) in a case where imaging is performed by the first insertion type irradiation device 18 or the second insertion type irradiation device 19. The worker performs an operation, diagnosis, or training thereof (which are collectively referred to as "work" in the present embodiment) by handling the probes 53 and 80 (refer to FIGS. 3 and 4) while looking into the surgical microscope 38. In the present embodiment, the control section 30 can acquire an image captured by the surgical microscope 38 and can display the image on the display section 36. The present invention can be realized without using the surgical microscope 38.

Figure 2:
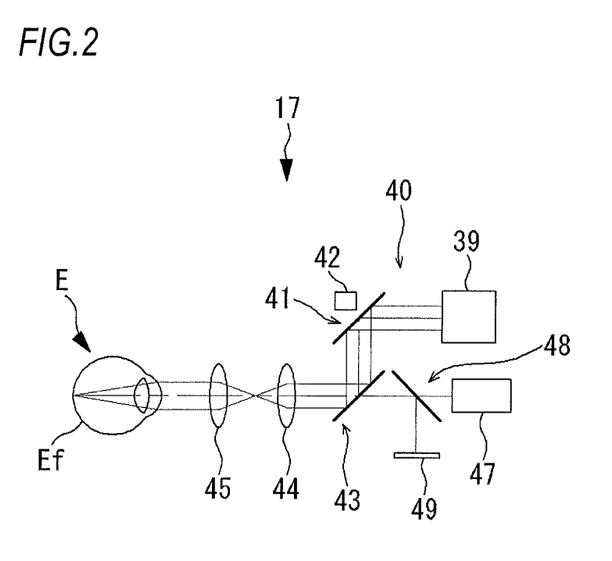
FIG. 2 is a diagram illustrating a schematic configuration of a noninvasive irradiation device 17.

With reference to FIG. 2, the noninvasive irradiation device 17 will be described. The noninvasive irradiation device 17 irradiates an internal tissue (the fundus Ef in the present embodiment) through the cornea of the eye E with measurement light which is guided by the coupler 12 and the unit switching portion 20. As a result, a tomographic image of the fundus Ef is captured in a noninvasive manner. The noninvasive irradiation device 17 includes a measurement optical system 40, an observation optical system 47, and a fixation target projection unit 48.

The measurement optical system 40 is provided with an optical scanner 41 at a position which is substantially conjugate to the pupil. The measurement optical system 40 scans the fundus Ef in a two-dimensional manner with the measurement light output from an end part 39 of fibers by driving the optical scanner 41 with a driving mechanism 42. As a result, an imaging position of a tomographic image on the fundus Ef is determined. The measurement light with which scanning is performed by the optical scanner 41 is applied to the eye E through a dichroic mirror 43 and lenses 44 and 45.

The observation optical system 47 is provided in order to acquire a front image of the fundus Ef. The observation optical system 47 of the present embodiment has a so-called scanning laser ophthalmoscope (SLO) configuration. More specifically, the observation optical system 47 includes an optical scanner and a light receiving element (not illustrated). The optical scanner transmits the measurement light (for example, infrared light) emitted from the light source through a dichroic mirror 48 so that the fundus Ef is scanned in a two-dimensional manner with the measurement light. The light receiving element receives the measurement light reflected from the fundus Ef via a cofocal aperture which is disposed at a position substantially conjugate to the fundus Ef.

In addition, the observation optical system 47 may have a configuration (a so-called fundus camera type configuration) in which a front image is acquired by performing wide irradiation with infrared light or the like. Further, the optical coherence tomography may also be used as the observation optical system. In other words, the optical tomographic imaging device 1 may acquire a front image of a tissue on the basis of data obtained by using the optical coherence tomography (the measurement light source 11, the coupler 12, the reference optical systems 13 and 14, and the like) in order to generate a tomographic image. The optical tomographic imaging device 1 may acquire a front image by using, for example, an integrated image obtained through integration of three-dimensional tomographic images in a depth direction, an integrated value of spectral data at respective positions in XY directions (two-dimensional directions on a plane perpendicular to an axial direction of the eye E), luminance data at respective positions in the XY directions in a specific depth direction, or a superficial capillary image.

The fixation target projection unit 49 is provided in order to guide a visual line direction of the eye E. In the present embodiment, the fixation target projection unit 49 includes a visible light source which generates visible light, and two-dimensionally changes a target presentation position. As a result, a visual line direction of the subject's eye E is changed, and thus an imaging part of the fundus Ef is changed. For example, if a fixation target is presented from the same direction as an imaging optical axis, a central part of the fundus Ef is set as an imaging part. If a fixation target is presented upward with respect to the imaging optical axis, an upper part of the fundus Ef is set as an imaging part. The fixation target projection unit 49 may employ various configurations. For example, a configuration may be employed in which a target position is adjusted depending on turned-on positions of LEDs which are arranged in a matrix. In addition, a configuration may be employed in which an optical scanner performs scanning with visible light. The fixation target projection unit 49 may be of an internal target type in which a fixation target is displayed from the inside of the device, and may be of an external target type in which a fixation target is displayed on the outside of the device.

Figure 3:
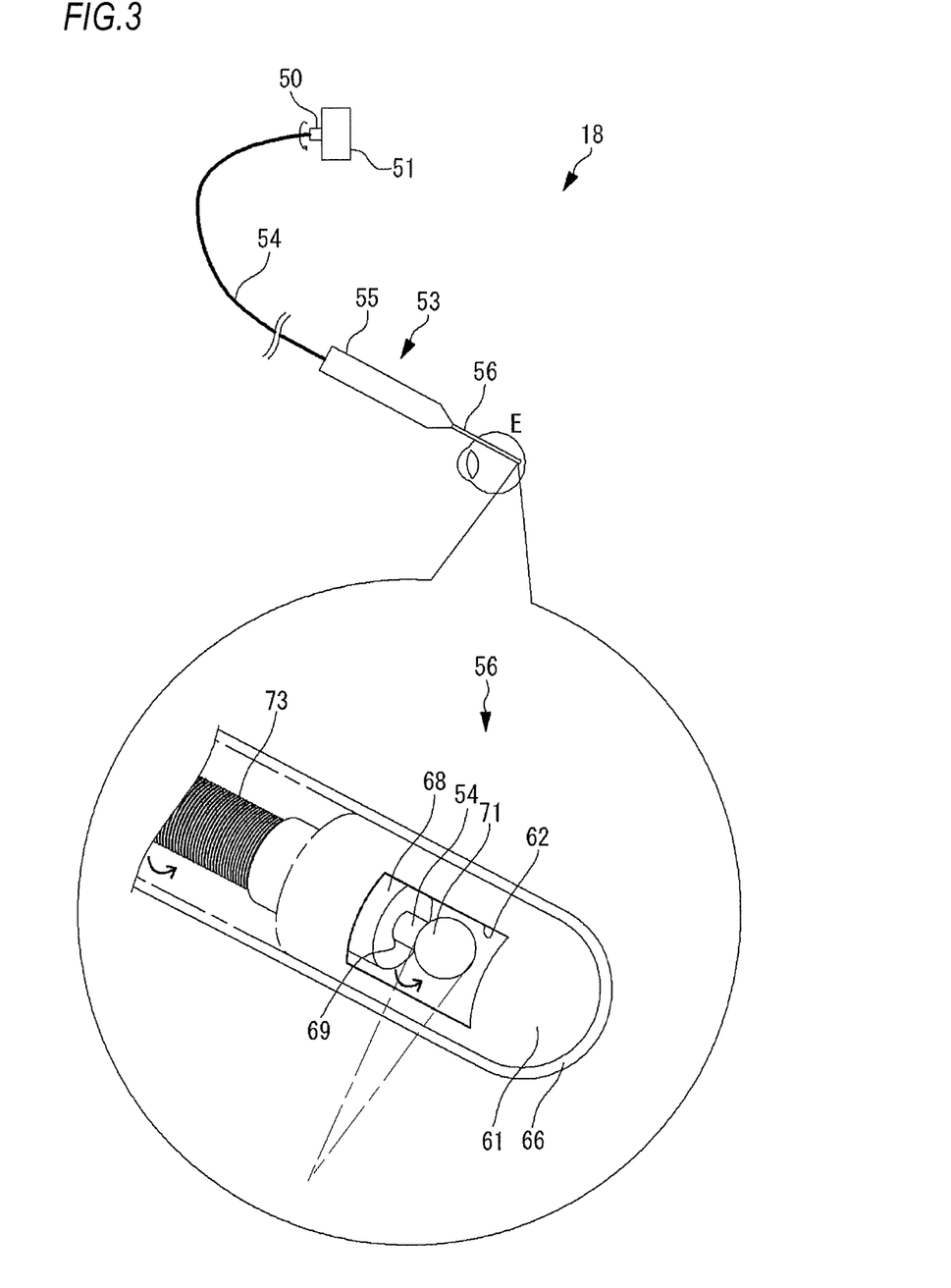
FIG. 3 is a diagram illustrating a schematic configuration of a first insertion type irradiation device 18.

With reference to FIG. 3, the first insertion type irradiation device 18 will be described. The first insertion type irradiation device 18 is used to capture a tomographic image of a tissue located in a circumferential direction of the needle 56 of the side imaging probe 53.

The side imaging probe 53 includes a fiber 54, a hand piece 55, and the needle 56. The fiber 54 guides measurement light which is guided from the coupler 12 of the measurement section 10, to a tip end of the needle 56. The fiber 54 is coated with a torque coil (not illustrated) and is freely rotated with reference to the hand piece 55. The hand piece 55 is a substantially tubular member which is held by the worker (for example, an examiner or an operator). The needle 56 is provided at a front end of the hand piece 55 and has an outer diameter smaller than an outer diameter of the hand piece 55. A tip end part of the needle 56 is inserted into the test object (the subject's eye E in the present embodiment). The fiber 54 is connected to a rear end part of the hand piece 55 and extends to the tip end part of the needle 56.

The first insertion type irradiation device 18 includes a fixing portion 50 and a fiber rotation motor 51. A rear end part (basal end part) of the fiber 54 is attachably and detachably attached to the fixing portion (for example, a connector) 50. The fiber rotation motor 51 can rotate the fixing portion 50 attached with the fiber 54, centering on an axis of the fiber 54. In other words, the fiber rotation motor 51 rotates the fiber 54 through rotation of the fixing portion 50 so as to perform scanning with the measurement light.

A detailed description will be made of a structure of the tip end part of the needle 56 of the side imaging probe 53. An outer cylinder 61, a cover 66, a holder 68, a light collecting portion 71, and the like are provided at the tip end part of the needle 56.

The outer cylinder 61 covers the periphery of the front end side of the fiber 4 (particularly, the periphery of the holder 68 and the light collecting portion 71). In the present embodiment, a shape of the outer cylinder 61 is a substantially tubular shape which has a hemispherical closed part at the front end. The outer cylinder 61 is made of a material blocking measurement light. An opening 62 having a predetermined width in the scanning direction (a direction around the axis) of measurement light is formed in the vicinity of the location where the light collecting portion 71 is disposed in the axial line direction in the outer cylinder 61. A light beam applied from the light collecting portion 71 is transmitted to the outside through the opening 62.

The cover 66 is made of a material through which measurement light is transmitted, and closes the outside of the outer cylinder 61. Therefore, the cover 66 prevents the blood, a tissue of the vitreous body, and the like from being entering the inside the outer cylinder 61 through the opening 62 and also allows light to be transmitted between the inside and the outside of the region of the opening 62.

The holder 68 is a substantially columnar member and is fixed to the outer cylinder 61. A through hole 69 into which the fiber 54 is rotatably inserted is formed at an axial core part of the holder 68. The holder 68 rotatably supports the fiber 54 in a state in which a position of the axis of the fiber 54 is made constant relative to the outer cylinder 61.

The light collecting portion 71 is provided at the front end part of the fiber 54. The light collecting portion 71 deflects light emitted from the front end part of the fiber 54 and also collects the light at a tissue of a test substance. In addition, the light collecting portion 71 collects reflected measurement light which is reflected from the tissue and causes the light be incident to the fiber 54. The light collecting portion 71 of the present embodiment deflects light at an angle of about 70 degrees with respect to the axial direction of the fiber 54, but may change a deflection angle as appropriate. A shaft 73 for preventing torsion of the fiber 54 is provided on the outer circumference of the fiber 54 which is located further toward the rear end side than the holder 68.

Figure 4:
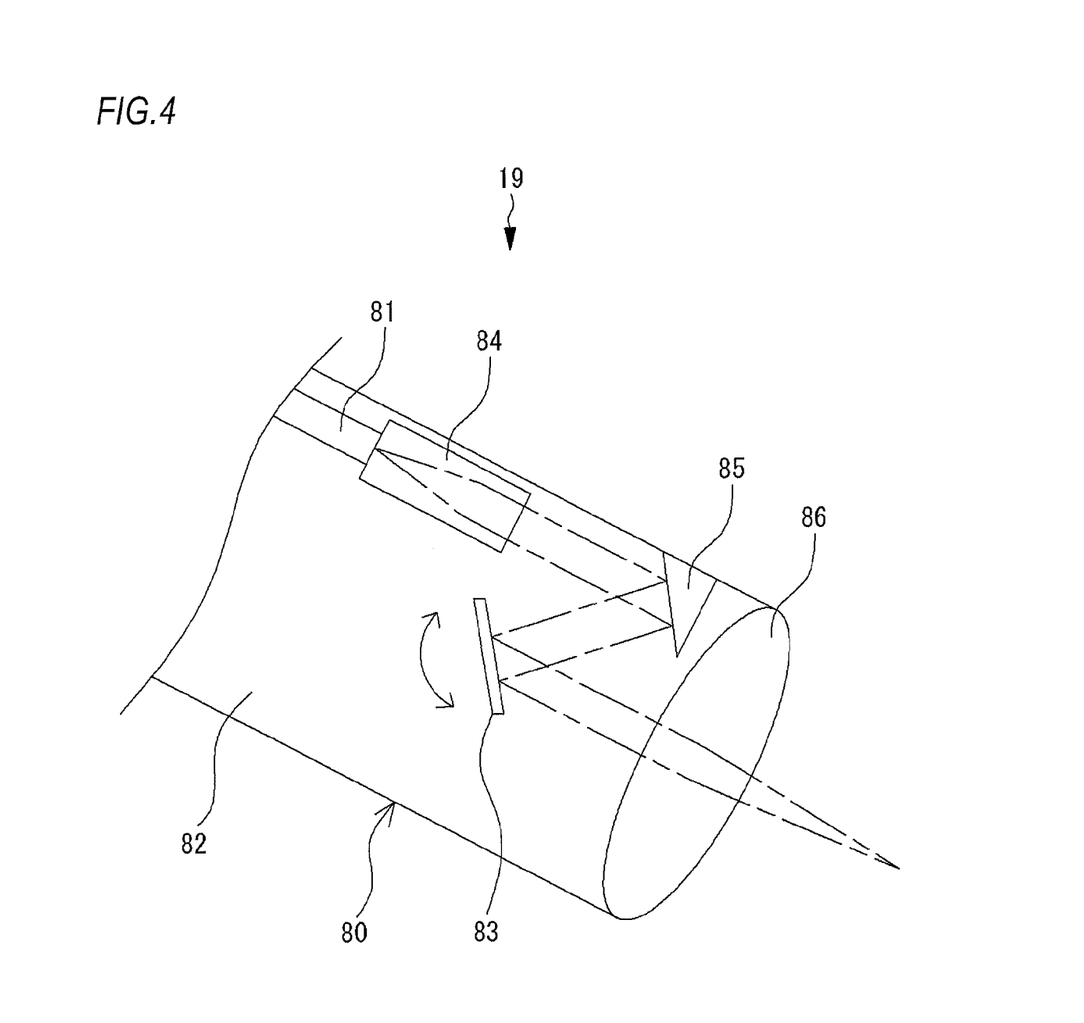
FIG. 4 is an enlarged view illustrating a part of a forward imaging probe 80 in a second insertion type irradiation device 19.

With reference to FIG. 4, the forward imaging probe 80 included in the second insertion type irradiation device 19 will be described. The forward imaging probe 80 includes a fiber 81, a hand piece (not illustrated), and a needle 82 in the same manner as the side imaging probe 53. However, the second insertion type irradiation device 19 performs scanning with measurement light by using a scanning portion 83 provided at the needle 82 instead of performing scanning with the measurement light through rotation of the fiber 81. The fiber 81 is attachably and detachably attached to a fixing portion (not illustrated).

The needle 82 of the fl9 is a tubular member. The needle 82 of the present embodiment is cylindrical but may be square tubular. The needle 82 may linearly extend, and may be bent or curved. A collimating portion 84, a reflective mirror 85, a scanning portion 83, and an objective lens 86 are provided around a tip end part inside the needle 82. The collimating portion 84 is attached at a front end part of the fiber 81, and collimates measurement light emitted from the front end of the fiber 81. The reflective mirror 85 reflects the measurement light collimated by the collimating portion 84 toward the scanning portion 83. The scanning portion 83 performs scanning with the measurement light guided from the collimating portion 84 on the tip end side of the needle 82. For example, various configurations such as galvanometer mirror and an acousto-optical element (AOM) may be used in the scanning portion 83. The objective lens 86 collects the measurement light with which scanning is performed by the scanning portion 83. Further, the reflected measurement light is returned along an optical path of the objective lens 86, the scanning portion 83, the reflective mirror 85, and the collimating portion 84 in this order and is incident to the fiber 81.

In addition, the configurations of the probes 53 and 80 are examples, and the configurations may be changed. For example, the present invention is applicable to a case where a probe provided with a configuration (for example, forceps) for treatment is used along with a configuration for capturing a tomographic image.

Figure 5:
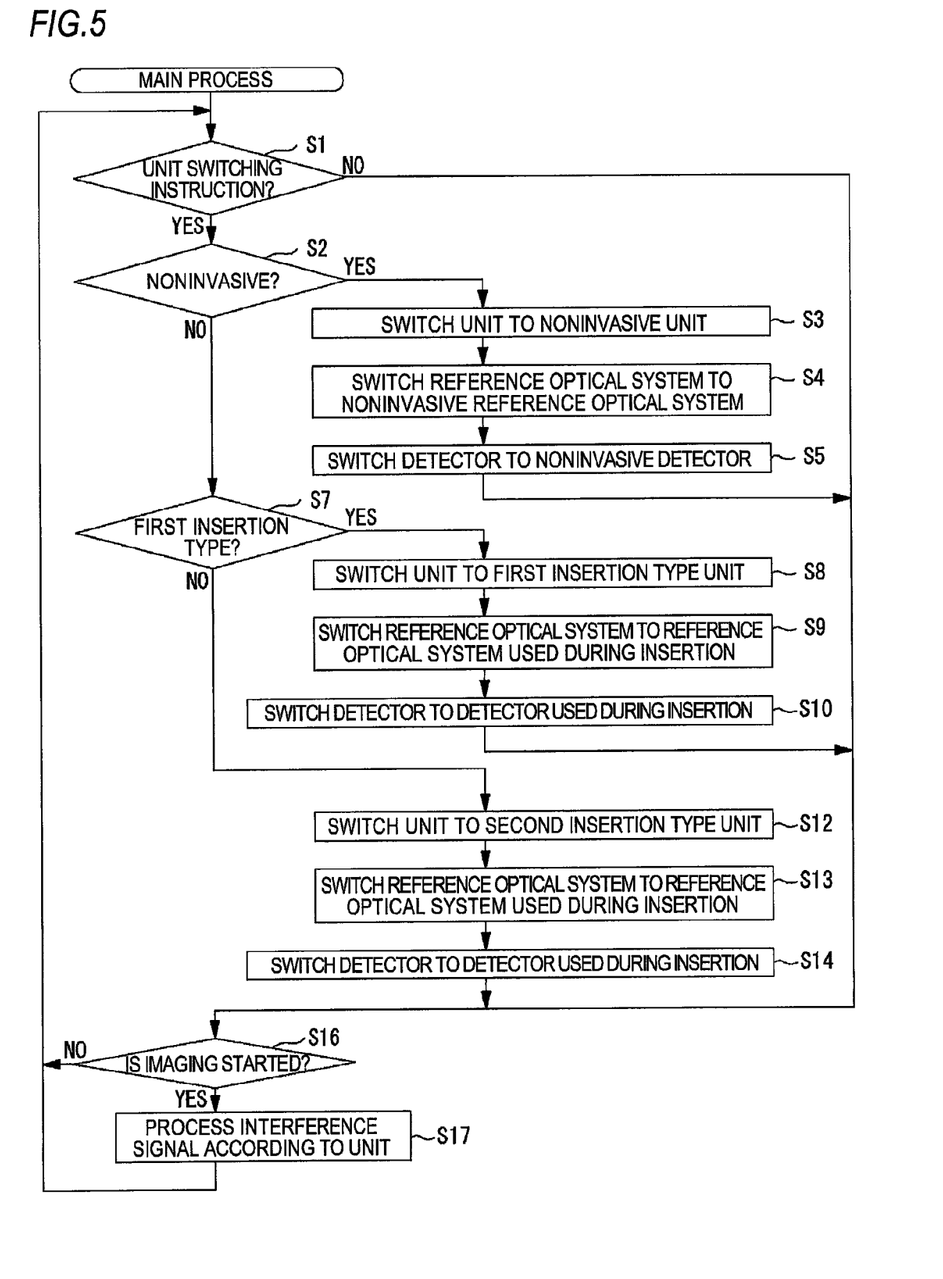
FIG. 5 is a flowchart illustrating a main process performed by the optical tomographic imaging device 1.

With reference to FIG. 5, a description will be made of a main process performed by the optical tomographic imaging device 1. The optical tomographic imaging device 1 of the present embodiment acquires an interference signal on the basis of interference light between reflected measurement light and reference light. A tomographic image of a tissue is acquired by processing the acquired interference signal. Further, the optical tomographic imaging device 1 can switch an irradiation device for irradiating a test object with measurement light. Therefore, the optical tomographic imaging device 1 can capture tomographic images in a plurality of aspects by using light emitted from the single measurement light source 11. If power is supplied to the optical tomographic imaging device 1, the CPU 31 of the control section 30 performs the main process illustrated in FIG. 5 according to a control process stored in the nonvolatile memory 34.

First, it is determined whether or not an instruction for switching the irradiation devices 17 to 19 is input (step S1). The switching instruction may be input from the operation section 37, and may be input from an external device via a network. If the switching instruction is not input (NO in step S1), the process proceeds to a determination in step S16.

If the switching instruction is input (YES in step S1), it is determined whether or not an irradiation device to be switched (an irradiation device used thereafter) is the noninvasive irradiation device 17 (step S2). If the irradiation device to be switched is the noninvasive irradiation device 17 (YES in step S2), an irradiation device connected to the coupler 12 is switched to the noninvasive irradiation device 17 by the unit switching portion 20 (step S3). A reference optical system connected to the coupler 12 is switched to the noninvasive reference optical system 13 by the reference light optical path switching portion 15 (step S4). A detector connected to the coupler 12 is switched to the noninvasive detector 22 by the detection switching portion 24 (step S5). The process proceeds to the determination in step S16.

If the irradiation device to be switched is not the noninvasive irradiation device 17 (NO in step S2), it is determined whether or not the unit is the first insertion type irradiation device 18 (step S7). If the irradiation device to be switched is the first insertion type irradiation device 18 (YES in step S7), an irradiation device connected to the coupler 12 is switched to the first insertion type irradiation device 18 by the unit switching portion 20 (step S8). A reference optical system connected to the coupler 12 is switched to the reference optical system 14 used for during insertion by the reference light optical path switching portion 15 (step S9). A detector connected to the coupler 12 is switched to the detector 23 used during insertion by the detection switching portion 24 (step S10). The process proceeds to the determination in step S16.

If the irradiation device to be switched is neither the noninvasive irradiation device 17 nor the first insertion type irradiation device 18 (NO in step S7), the irradiation device to be switched is the second insertion type irradiation device 19. In this case, an irradiation device connected to the coupler 12 is switched to the second insertion type irradiation device 19 by the unit switching portion 20 (step S12). A reference optical system connected to the coupler 12 is switched to the reference optical system 14 used for during insertion by the reference light optical path switching portion 15 (step S13). A detector connected to the coupler 12 is switched to the detector 23 used during insertion by the detection switching portion 24 (step S14). The process proceeds to the determination in step S16.

Next, it is determined whether or not an instruction for starting capturing of a tomographic image is input (step S16). If the instruction for starting capturing a tomographic image is not input (NO in step S16), the process returns to the determination in step S1. If the instruction for starting capturing of a tomographic image is input from the operation section 37 or the like (YES in step S16), a tomographic image starts being captured by controlling the measurement light source 11 and the like, and a captured front image is acquired from the surgical microscope 38 (refer to FIG. 1) or the observation optical system 47 (refer to FIG. 2). Further, the interference signal detected by the detectors 22 and 23 is processed depending on an irradiation device which is being used (step S17). Specifically, the CPU 31 performs a well-known spectrum analysis process such as Fourier transform on the detected interference signal so as to acquire information regarding the part in the depth direction (vibration intensity distribution in the depth direction), irradiated with the measurement light. The CPU 31 acquires a two-dimensional tomographic image by acquiring the information in the depth direction while performing scanning with the measurement light. A more appropriate tomographic image is acquired by performing the above-described process on the interference signal according to an irradiation device which is being used. The process returns to the determination in step S1. In addition, the acquired tomographic image data is stored in the nonvolatile memory 34. If the supply of power to the optical tomographic imaging device 1 is stopped, the main process is finished.

Figure 6:
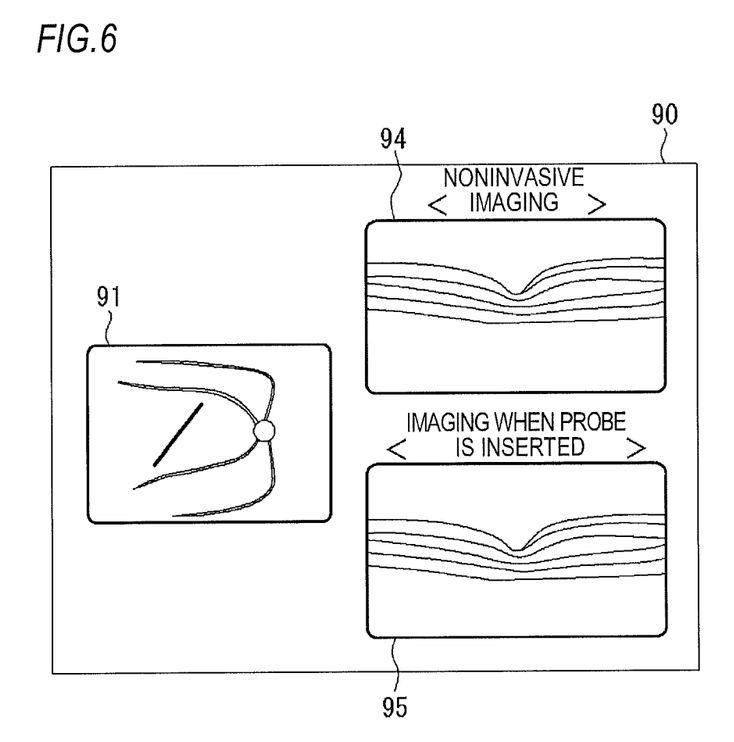
FIG. 6 is a diagram illustrating an example of a display aspect of a tomographic image on a display section 36.

With reference to FIG. 6, a description will be made of a display aspect of a tomographic image on the display section 36 in the present embodiment. As illustrated in FIG. 6, the CPU 31 displays a noninvasive captured image 94 which is captured by the noninvasive irradiation device 17 and a probe insertion captured image 95 which is captured by the insertion type irradiation devices 18 and 19 side by side on a tomographic image display screen 90. Specifically, the CPU 31 stores captured tomographic image data in the nonvolatile memory 34. In a case where a tomographic image is being captured by the noninvasive irradiation device 17, if data regarding tomographic images of the same test substance captured by the insertion type irradiation devices 18 and 19 is stored, the stored probe insertion captured image 95 is displayed by the side of the noninvasive captured image 94 which is being captured in real time. In addition, in a case where tomographic images are being captured by the insertion type irradiation devices 18 and 19, if data regarding tomographic images of the same test substance captured by the noninvasive irradiation device 17 is stored, the stored noninvasive captured image 94 is displayed by the side of the probe insertion captured image 95 which is being captured in real time. In addition, if image capturing is finished, the noninvasive captured image 94 stored in the nonvolatile memory 34 and the probe insertion captured image 95 may be displayed side by side. Therefore, the worker can perform image capturing using different irradiation devices with simple work and can perform effective diagnosis or treatment by comparing a plurality of captured tomographic images with each other. Further, the optical tomographic imaging device 1 may display an image captured by the first insertion type irradiation device 18 separately from an image captured by the second insertion type irradiation device 19.

In addition, in the present embodiment, a front image 91 of the test substance (for example, the fundus Ef) is also displayed on the display section 36. In a case where the front image 91 captured by the observation optical system 47 is displayed, the CPU 31 displays an irradiation position (scanning position) of measurement light for capturing the noninvasive captured image 94 on the front image 91 in a superimposed manner. Further, the front image 91 captured by the surgical microscope 38 includes an irradiation position (that is, an irradiation position of aiming light applied on the same axis as an axis of the measurement light) for capturing the probe insertion captured image 95. Therefore, the worker can accurately recognize a position on the test substance at which a tomographic image is captured.

In addition, the CPU 31 may perform positioning of the front image 91 captured by the observation optical system 47 and the front image 91 captured by the surgical microscope 38. The positioning may be performed, for example, by performing a well-known image process on the two front images 91 so as to extract feature points, and by adjusting a position, an angle, and a size of at least one of the two front images 91 so that positions, angles, and sizes of the extracted feature points match each other. As a result of the positioning, a position where the noninvasive captured image 94 is captured and a position where the probe insertion captured image 95 is captured can be displayed on the same front image 91. Successively, the CPU 31 displays one of the front image 91 captured by the observation optical system 47 and the front image 91 captured by the surgical microscope 38 on the display section 36. More preferably, the front image 91 which is being captured in real time is displayed on the display section 36, but the stored front image 91 may be displayed. The CPU 31 displays both of the position where the noninvasive captured image 94 is captured and the position where the probe insertion captured image 95 is captured on one front image 91 which is displayed. Therefore, the worker can easily recognize the tomographic images 94 and 95 captured by different irradiation devices, and positions on the test substance where the respective tomographic images 94 and 95 are captured, by using the tomographic image display screen 90.

As described above, the optical tomographic imaging device 1 of the present embodiment switches the irradiation devices 17 to 19 which guide a light beam emitted from the measurement light source 11, with the unit switching portion 20. Therefore, the optical tomographic imaging device 1 can acquire tomographic images in a plurality of aspects by using measurement light emitted from the single measurement light source 11. The worker can obtain the tomographic images in a plurality of aspects without switching a device or replacing a probe. Particularly, in the present embodiment, the noninvasive irradiation device 17 and the insertion type irradiation devices 18 and 19 can be switched to each other. In this case, the worker can easily cause the optical tomographic imaging device 1 to perform noninvasive imaging which is frequently used during diagnosis and insertion type imaging which is frequently used during treatment, without requiring time and effort to preparing two devices.

The optical tomographic imaging device 1 of the present embodiment displays a plurality of (two or more) tomographic images which are respectively acquired by the irradiation devices 17 to 19 side by side on the display section 36. Therefore, the worker the worker can perform image capturing using different irradiation devices 17 to 19 with simple work and can perform effective diagnosis or treatment by comparing a plurality of captured tomographic images with each other.

The unit switching portion 20 of the present embodiment is an optical switch which changes a path of a light beam emitted from the measurement light source 11. In this case, the optical tomographic imaging device 1 can switch the irradiation devices 17 to 19 to be used with a simple configuration.

The optical tomographic imaging device 1 of the present embodiment includes the reference light optical path switching portion 15 which switches a path along which reference light separated by the coupler 12 is guided among a plurality of paths of the reference light. In this case, the optical tomographic imaging device 1 can easily switch an optical path length of the reference light to an optical path length suitable for an irradiation device to be used.

The optical tomographic imaging device 1 of the present embodiment includes the detection switching portion 24 which switches a detector to which interference light generated by the coupler 12 is incident among a plurality of detectors which detect an interference signal. In this case, the optical tomographic imaging device 1 can detect the interference signal by using a detector suitable for an irradiation device to be used.

Needless to say, the present invention is not limited to the above-described embodiment and may be variously modified. The optical tomographic imaging device 1 of the embodiment includes the unit switching portion 20 which switches the irradiation devices 17 to 19, the reference light optical path switching portion 15 which switches the reference optical systems 13 and 14, and the detection switching portion 24 which switches the detectors 22 and 23. However, the number or positions of disposed switching portions can be changed. For example, in a case where common reference optical system and detector can be used for a plurality of irradiation devices, the measurement light source 11, the reference optical system, and the detector may be all used in common, and only the unit switching portion 20 switching the irradiation devices 17 to 19 may be provided. In this case, the configurations which can be used in common are increased compared with the above-described embodiment, and thus a device configuration can be simplified. In other words, only one or two of the unit switching portion 20, the reference light optical path switching portion 15, and the detection switching portion 24 may be used.

Needless to say, the number and the types of a plurality of irradiation devices which are switchable can be changed. For example, the optical tomographic imaging device may switch a plurality of insertion type irradiation devices without including the noninvasive irradiation device 17. The present invention is also applicable to a case where the same type of irradiation device is switched. In addition, different types of irradiation devices such as a surgical microscope type OCT irradiation device in which some configurations of the optical coherence tomography are mounted in the surgical microscope 38 may be included in switchable irradiation devices.

In the embodiment, switches for switching the irradiation devices 17 to 19, the reference optical systems 13 and 14, and the detectors 22 and 23 are all optical switches. However, an optical path may be switched by using configurations other than the optical switch. For example, the optical tomographic imaging device may switch an optical path by moving an optical fiber with an actuator.

The unit switching portion 20 of the embodiment switches a guide destination of measurement light separated by the coupler 12. However, in a case where dividing means for dividing light emitted from the measurement light source 11 is provided in each of the irradiation devices 17 to 19, a guide destination of light before being divided may be switched by the unit switching portion 20.

In the present embodiment, the control section 30 may acquire an angiographic image of the inside of a test object, captured in advance by a medical image device which can capture a front image of the inside of the test object. In addition, the control section 30 may display the angiographic image of the inside of the test object by the side of a probe insertion captured image of the test object acquired by the control section 30 on a screen of the display section. For example, when a tomographic image is captured by probe OCT, there is a case where it may be hard for a work or the like to recognize a position where the tomographic image is captured in an observation method (for example, a method of performing observation with a surgical microscope or a method of performing observation with the naked eyes) based on observation light which is applied to a tissue inside a test object from the outside of the test object and is reflected from the tissue of the test object. For example, there may be a case where favorable observation of the fundus may be obstructed due to the opacity of the crystal lens in the cataract eye. In contrast, there is a case where blood vessels of a shield portion (for example, an opacity portion of the crystal lens) which are hard to observe in observation based on observation light reflected from the tissue of the test object may be imaged in an angiographic image of the test object inside. For this reason, by displaying the angiographic image of the test object inside, information regarding a location which is hard to observe with a surgical microscope or the naked eyes may be supplemented by using information regarding the angiographic image. As a result, it becomes easier for the worker or the like to recognize a position where a tomographic image is captured by the probe OCT.

What is claimed is:

1. An optical tomographic imaging device configured to acquire a tomographic image of a tissue of an object, the device comprising:
   a dividing device configured to divide a light beam emitted from a light source into measurement light and reference light;
   a combining device configured to combine the measurement light, which is separated by the dividing device and is reflected from the tissue, with the reference light separated by the dividing device so as to generate interference light for acquiring the tomographic image;
   a plurality of irradiation devices, each of the plurality of irradiation devices being configured to guide the measurement light output from the dividing device and irradiate the tissue with the measurement light: and
   a switching device configured to switch the plurality of irradiation devices from one to another and select one of the plurality of irradiation devices to cause the selected irradiation device to irradiate the measurement light output from the dividing device with tissue.

2. The optical tomographic imaging device according to claim 1, wherein the plurality of devices includes:
   a noninvasive irradiation device configured to irradiate an internal tissue with the measurement light through a cornea of an eye from the outside of the eye which is the object, and
   an insertion type irradiation device configured to irradiate the internal tissue with the measurement light from a probe which is inserted into the eye.

3. The optical tomographic imaging device according to claim 1, further comprising:
   a display controller configured to control a display to display two or more images of a plurality of the tomographic images which can be respectively acquired by the plurality of irradiation devices.

4. The optical tomographic imaging device according to claim 1, wherein the switching device includes an optical switch configured to change a path of the light beam emitted from the light source.

5. The optical tomographic imaging device according to claim 1, further comprising:
   a plurality of paths, each of the plurality paths being configured to guide the reference light separated by the dividing device,
   a reference light path switching device configured to switch the plurality of paths from one to another and select one of the plurality of paths to cause the selected path to guide the reference light separated by the dividing device.

6. The optical tomographic imaging device according to claim 1, further comprising:
   a plurality of detectors, each of the plurality of detectors being configured to receive the interference light generated by the combining device to a detector; and
   a detection switching device configured to switch the plurality of detectors from one to another and select one of the plurality of detectors to cause the selected detector to receive the interference light.

* * * * *